United States Patent
Davis

(10) Patent No.: US 9,102,465 B2
(45) Date of Patent: Aug. 11, 2015

(54) CONTAINER AND METHOD FOR STORING ANIMAL WASTE AND CONTROLLING ASSOCIATED ODOR

(76) Inventor: Gail Elizabeth Davis, Houston, TX (US)

( * ) Notice: Subject to any disclaimer, the term of this patent is extended or adjusted under 35 U.S.C. 154(b) by 40 days.

(21) Appl. No.: 12/657,581

(22) Filed: Jan. 22, 2010

(65) Prior Publication Data

US 2011/0180008 A1 Jul. 28, 2011

(51) Int. Cl.
| | |
|---|---|
| B65D 33/08 | (2006.01) |
| B65F 1/00 | (2006.01) |
| A61L 9/014 | (2006.01) |
| A61L 9/16 | (2006.01) |

(52) U.S. Cl.
CPC ............... *B65F 1/0006* (2013.01); *A61L 9/014* (2013.01); *A61L 9/16* (2013.01); *A61L 2209/14* (2013.01)

(58) Field of Classification Search
CPC ............................ A01K 23/00; A01K 23/005
USPC ................. 119/165–170, 867; D30/161–162; 220/359.2; 383/9, 10, 16, 91
See application file for complete search history.

(56) References Cited

U.S. PATENT DOCUMENTS

| | | | | |
|---|---|---|---|---|
| 2,394,335 A | * | 2/1946 | Shapiro | 383/9 |
| 2,861,735 A | * | 11/1958 | Faltin | 383/11 |
| 3,286,826 A | * | 11/1966 | Stoll | 294/1.3 |
| 3,487,814 A | * | 1/1970 | Ingebritsen | 119/497 |
| 3,986,744 A | * | 10/1976 | Krogstad et al. | 294/1.3 |
| 4,102,487 A | * | 7/1978 | Soto | 383/27 |
| 4,103,952 A | * | 8/1978 | Thompson | 294/1.3 |
| 4,518,115 A | * | 5/1985 | Sedwick | 229/117.14 |
| 4,800,677 A | | 1/1989 | Mack | |
| 4,840,611 A | * | 6/1989 | Van Erden et al. | 493/213 |
| 4,848,929 A | | 7/1989 | Rawl | |
| 4,854,501 A | | 8/1989 | Ricci | |
| 4,974,893 A | * | 12/1990 | Grahn | 294/1.3 |
| 4,981,104 A | * | 1/1991 | Goodwin | 119/168 |
| 5,129,364 A | | 7/1992 | Pirkle | |
| 5,174,462 A | * | 12/1992 | Hames | 220/87.1 |
| 5,186,384 A | * | 2/1993 | Nelson | 229/122 |
| 5,346,312 A | | 9/1994 | Mabry et al. | |
| 5,425,887 A | | 6/1995 | Lam et al. | |
| 5,511,513 A | * | 4/1996 | Baron et al. | 119/163 |
| 5,511,883 A | * | 4/1996 | Clark et al. | 383/22 |
| 5,564,762 A | * | 10/1996 | Ring | 294/1.3 |
| 5,829,671 A | * | 11/1998 | Hawk | 229/103 |
| 6,126,215 A | * | 10/2000 | Jahns | 294/1.3 |
| 6,298,808 B1 | * | 10/2001 | Crafton et al. | 119/165 |
| 6,382,131 B1 | * | 5/2002 | McGivern | 119/165 |

(Continued)

*Primary Examiner* — Rob Swiatek
*Assistant Examiner* — Ebony Evans

(57) ABSTRACT

Containers and methods for storing animal waste, such as feline or canine waste, human waste, and/or soiled waste products, and controlling associated odor are described. A container having a compressible body with an open top, is provided, the body of the container including a material substantially impermeable to vapor to prevent permeation of odor through the body. Waste is deposited within the container, and a closing member is used to secure the open top of the container in a closed position to at least partially prevent exodus of air carrying the odor from the interior. A filtering member secured within the interior of the container further removes odor to minimize exodus of odor from the container into the surrounding environment. The container can thereby effectively store waste while controlling associated odors, enabling indoor storage, or similar temporary retention of the contained waste until outdoor disposal becomes convenient.

21 Claims, 2 Drawing Sheets

(56) References Cited

U.S. PATENT DOCUMENTS

| | | |
|---|---|---|
| 6,453,845 B1 * | 9/2002 | Efrati et al. .................. 119/168 |
| 6,506,184 B1 | 1/2003 | Villefrance |
| 6,695,826 B2 | 2/2004 | Villefrance |
| 6,761,130 B1 * | 7/2004 | Vicknair ...................... 119/165 |
| 6,945,193 B1 * | 9/2005 | Tanner et al. ................ 119/165 |
| 8,012,554 B2 * | 9/2011 | Shelley et al. ............... 428/36.6 |
| 2003/0100870 A1 | 5/2003 | Villefrance |
| 2004/0200424 A1 * | 10/2004 | Stolpe .......................... 119/165 |
| 2004/0200890 A1 * | 10/2004 | Mesly .......................... 229/101 |
| 2005/0115511 A1 * | 6/2005 | Lange .......................... 119/169 |
| 2006/0111682 A1 | 5/2006 | Schena et al. |
| 2009/0194033 A1 | 8/2009 | Modlin |
| 2013/0220226 A1 * | 8/2013 | Molzan ........................ 119/161 |

\* cited by examiner

CONTAINER AND METHOD FOR STORING ANIMAL WASTE AND CONTROLLING ASSOCIATED ODOR

FIELD

The present invention relates, generally, to disposable containers and methods for storing solid waste, such as fecal matter from felines, canines, humans, or other animals, clumped cat litter, soiled pet mats or other pet products, diapers, and other similar objects, and controlling the odor associated therewith until proper disposal.

BACKGROUND

Domestic felines and similar house pets instinctively seek out a suitable location within a structure to excrete solid waste, and will typically reuse this location. Generally, felines react adversely to the odor produced by feces and urine and are prone to select locations where the waste can be buried or similarly covered. As such, most domesticated cats will reliably utilize a litter box to contain excreted waste products.

A litter box, as its name implies, is a container that is normally rigid, durable, reusable, and at least partially filled with cat litter, which includes a loose, granular material that absorbs moisture and odors. Most commonly, cat litter is formed from clay, though paper and silicon-based materials are also used. Many varieties of cat litter include selected chemicals or compounds to enhance the deodorizing or moisture-absorbing properties of the litter.

Though somewhat effective, the odor-reduction properties of a litter box are limited. To prevent the odors associated with animal waste from permeating throughout a structure, waste from a litter box must be frequently removed for disposal. However, simply moving animal waste from a litter box to a conventional indoor waste receptacle does not remove the source of odor from the structure. As such, animal waste must be carried to an outdoor receptacle for disposal. Undertakings of this nature are often tedious and inconvenient, especially for pet owners that live in condominiums, high-rises, apartment complexes, and other locations where use of the nearest outdoor waste receptacle may require traveling a significant distance while carrying odorous animal waste.

Similarly, when caring for young children and/or incontinent adults, diapers and other waste disposal products must also frequently be retained indoors until a time when disposal external to a structure is convenient. Likewise, canines and similar pets, when retained indoors, can be trained to utilize disposable pads or similar absorbent products, which must often be retained indoors prior to disposal outside of the structure. Additionally, when keeping canines and similar outdoor pets, or when walking or otherwise traveling with a pet, the odorous waste from such animals must often be contained for aesthetic, environmental, and/or legal reasons, until disposal in a suitable receptacle is possible.

A need exists for a container and method for storing animal and/or human waste, as well as clumped cat litter, soiled pet products, diapers, and similar objects, and controlling the associated odor, thereby enabling storage and/or transport of the waste prior to disposal, while preventing the exodus of odor from the container.

A need also exists for generally inexpensive, disposable containers that can control odor through vapor impermeability, a closable top, and an internal filtering and/or deodorizing member.

A further need exists for a container and method for storing waste and controlling associated odors that is compact, easily transportable and stored, and readily accessible to a user.

The present invention meets these needs.

BRIEF DESCRIPTION OF THE DRAWINGS

In the detailed description of the embodiments of the invention presented below, reference is made to the accompanying drawings, in which.

Figure 1:
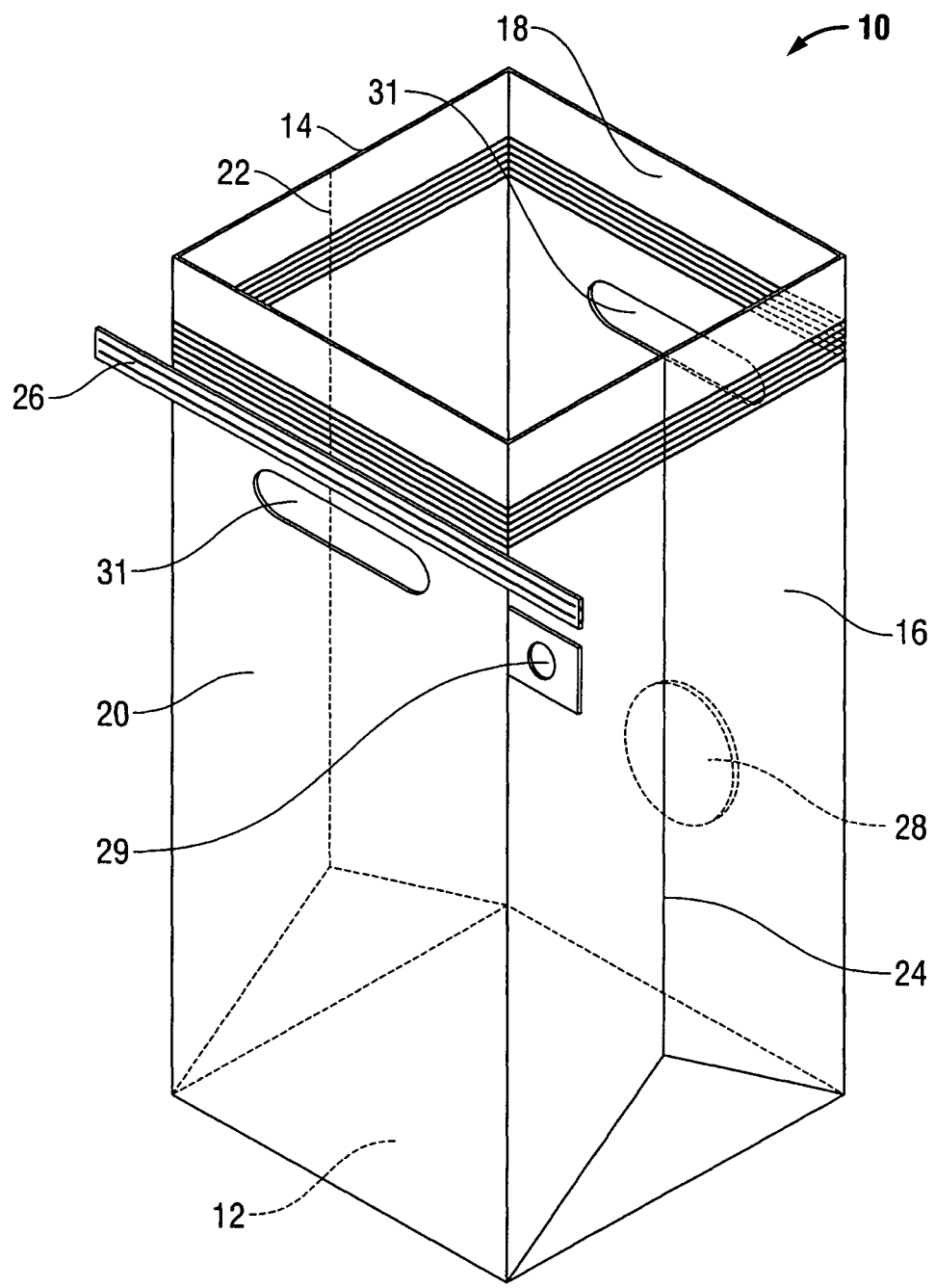
FIG. 1 depicts an embodiment of a container for storing animal waste and controlling associated odor.

The depicted embodiments of the invention are described below with reference to the listed Figures.

DETAILED DESCRIPTION OF THE EMBODIMENTS

Before explaining the disclosed embodiments of the invention in detail, it is to be understood that the present invention is not limited to the particular embodiments depicted or described, and that the invention can be practiced or carried out in various ways.

The present invention relates, generally, to a container for storing animal and/or human waste, and waste containment objects, as described above, and controlling odors associated therewith, and methods of use for such a container. The materials from which the container is formed can vary, depending on the nature of the waste to be contained, the liquid content of the waste, the length of storage intended, the location where the container and waste is to be stored, and other factors. In an embodiment of the invention, the container can include a compressible body, formed from generally flexible, foldable, and/or compressible materials for storing animal waste. For example, the body of the container can be formed from any combination of paper, plastic, rubber, aluminum, textile materials, or combinations thereof. Generally, the body of the container will include one or more materials that are substantially impermeable to vapor to prevent passage of air carrying odors associated with the contained waste from penetrating through the container walls to contaminate the surrounding area. One or more of the materials from which the container is formed can also be generally liquid impermeable, for containing waste that includes one or more liquid components. In addition, embodiments of the container can be used to dispose of clumped litter containing solid or liquid waste, soiled pet mats or similar pet products, diapers, and the like.

In selected embodiments of the invention, the container can be formed from a single generally inexpensive, vapor impermeable layer; however, in other embodiments of the invention, the container can be formed from two or more layers of material. For example a usable container could include an outer layer formed from paper, foil, or a similar disposable covering and/or decorative material, and an inner material functioning as a vapor impermeable liner, such as a layer of plastic, for preventing the permeation of odor therethrough. In a further embodiment of the invention, the container can be formed from one or more biodegradable materials to facilitate disposal while minimizing negative environmental impact.

While the container can be provided with any shape or dimensions, depending on the quantity and type of waste to be stored and the space within which the container will be placed while storing the waste, in an embodiment of the invention, the compressible body of the container can include a walled bag shape, having a base and one or more side surfaces, with an open top, thereby defining an interior for containing waste. In a further embodiment of the invention, the base can have sufficient rigidity such that the container can be placed in a freestanding orientation during storage.

In use, animal waste, such as feces from a feline, clumped cat litter containing urine or other waste, and/or any excess cat litter or other material gathered using a scoop or similar waste carrying apparatus can be placed into the interior of the container through the open top. In an embodiment of the invention, the open top of the container can be wider than the base, such as twice the width of the base, for accommodating at least partial entry of a scoop or similar waste carrying apparatus to prevent spillage of waste. In other embodiments of the invention, the container can include a generally rectangular shape, having two sets of parallel sides. The container can be provided with any desirable dimensions, including dimensions suitable for accommodating waste from canines, humans, or other animals, or for accommodating diapers and/or pet waste products, as described previously. For example, an embodiment of the invention can include an enlarged length and width for accommodating soiled disposable pet pads containing solid and/or liquid waste from a canine.

Once waste has been placed within the container, the open top can be secured in a closed position through use of a closing member, which can include any manner of tie or similar flexible member, an elastic member, a generally rigid member usable to roll or compress the open top into a closed position, or other methods of closure known in the art. For example, the container can be provided with a folding tap used to fold and/or roll two sides of the container together, interlocking fasteners, such as ZipLoc® technology, adhesives, zippers, snaps, buttons, buckles, hook-and-loop fasteners, such as Velcro®, and/or other similar methods of securing and/or fastening. The vapor impermeable material of the container then prevents exodus of odor from the interior while the container is transported or stored at a selected location, until disposal in an outdoor receptacle or similar suitable site for receiving waste.

To further control odor associated with the stored animal waste, the interior of the container can be provided with a filtering member, such as a charcoal filter, a deodorizing member, which can include or one or more scented or deodorizing compounds, or combinations thereof. Additionally, in an embodiment of the invention, the material of the container body can be scented or provided with a fragrant and/or deodorizing compound. Removal and/or concealment of odor within the container by the filtering or deodorizing member enhances the effectiveness of the vapor impermeable material within the container body.

To facilitate transport of the container once filled and/or storage or hanging of the container when empty, a handle can be provided, which can include a protruding member, or simply one or more holes disposed through a portion of the container for accommodating hands or fingers. Similarly, the handle, or other orifices within or protruding from the body of the container can be provided for accommodating dog leases or other elongate members for facilitating transport of the container. Optionally, a disposable glove, scoop, or other implement for handling waste can be provided within the container, and/or attached to the orifice or body of the container.

Referring now to FIG. 1, an embodiment of a container (10) usable within the scope of the present invention is shown. The depicted container (10) is shown as a multi-walled bag having a base (12) and four sides, which for reference purposes are hereafter referred to as left side (14), back side (18), right side (16), and front side (20). It should be understood that while FIG. 1 depicts the container (10) as a four-sided bag, any shape or dimensions that define a container with at least one closable opening are usable.

The four sides (14, 16, 18, 20) and base (12) define an open top and an interior of the container (10) usable to receive animal waste and/or similar odorous objects. Each of the sides (14, 16, 18, 20) is shown projecting upward from the base (12), generally parallel to each opposing side, however in an embodiment of the invention, the sides (14, 16, 18, 20) can extend upward at an angle to provide the open top of the container (10) with a width greater than that of the base (12), for accommodating a scooping apparatus or similar waste carrying member used to transport and deposit waste. It should be understood that embodiments of the invention can include any shape or dimensions. Each of the sides (14, 16, 18, 20) and/or the base (12) can be formed from one layer or multiple layers of generally compressible materials, such as paper, plastic, aluminum foil, textile materials, other similar materials, or combinations thereof, such that the container (10) can be readily folded or otherwise compressed for storage both before and during use. For example, FIG. 1 depicts the left side (14) having a first series of folds (22), and the right side (16) having a second series of folds (24), usable to fold the container (10) into a generally flat shape for storage prior to use. Similarly, the folds (22, 24) are usable when closing the open top of the container (10) to enclose waste therein.

In an embodiment of the invention, the container can be foldable or otherwise compressible to provide the container with extremely compact dimensions, such as through use of "origami-style" folding or any other folding or compression known in the art, to facilitate storage and transport, such as when it is desirable to carry one or more disposable waste containers when walking a dog, traveling with an infant, or other similar activities during which a need to contain odorous waste may arise. In a further embodiment of the invention, the base (12) can be provided with sufficient rigidity to enable the container (10) to be placed in a freestanding orientation, which can facilitate deposition of waste into the container (10) as well as storage of the container after placing waste therein. For example the base (12) could be formed from a material having greater rigidity than that of the sides (14, 16, 18, 20), provided with a thickness greater than that of one or more of the sides (14, 16, 18, 20), provided with an additional layer or insert of generally rigid material, such as cardboard or plastic, other similar techniques, or combinations thereof.

In an embodiment of the invention, each of the sides (14, 16, 18, 20) and/or the base (12) can be lined with a vapor and/or liquid impermeable material, such as plastic or rubber. For example, the exterior of the container (10) could be formed from paper, foil, or a similar material, while the interior of the container (10) is lined with plastic, to facilitate containment of odors produced by waste contained therein, while also preventing seepage of liquid components of waste through the container (10). In other embodiments of the invention, the sides (14, 16, 18, 20) and/or the base (12) can include a single layer of vapor and/or liquid impermeable material.

The container (10) is shown having a closing member (26) secured close to the top of the front side (20) to enable the open top of the container (10) to be closed after waste is placed within the interior. For example, the top of the front side (20) and the back side (18) can be compressed into contact, facilitated by the folds (22, 24) within the left and right sides (14, 16), and the closing member (26) can be rolled and/or folded downward, thereby wrapping the front and back sides (20, 18) about the closing member (26) to secure the open top in a closed position. While FIG. 1 depicts the closing member (26) as a generally rigid, rectangular member able to engage the front and back sides (20, 16) of the container (10) by rolling and/or folding, other closing members are also usable, such as flexible and/or elastic members, one or more adhesives, fasteners, or other similar closure elements known in the art.

FIG. 1 further depicts an orifice (29) disposed along a side of the container (10), which can include any manner of grommet or similar reinforcement, one or more fasteners, or similar objects. In use, the orifice (29) can have a leash of an animal, a belt or belt loop, a keychain, a strap of a bag, purse, or backpack, or similar elongate member inserted therethrough to facilitate transport and carrying of the container (10) prior to use, and optionally, after depositing waste into the container (10). In an embodiment of the invention, the orifice (29) can be positioned such that it is accessible when the container (10) is folded, to facilitate transport of the container (10) in a space-saving manner prior to use. FIG. 1 also depicts a handle (31) near the top of the container (10), which includes an elongate orifice disposed through each of the front side (20) and the back side (18) that align when the container (10) is folded for storage and/or when the container is closed. Other types of handles, such as an exterior member disposed on one or more sides of the container, are also usable.

A filtering member (28) is shown secured to the interior of the back side (16), such that air within the container (10) is filtered or otherwise exposed to the filtering member (28). The filtering member (28) can include any type of filtration device, such as a charcoal filter, and/or any type of deodorizing or scented compound. To further control the permeation of odor from within the container (10), the filtering member (28) can reduce and/or eliminate at least a portion of odors associated with waste stored within the container (10). Use of the filtering member (28) can facilitate multiple uses of the container (10) by enabling a user to reopen the container to deposit additional waste within without permitting a significant quantity of odor to exit the container (10). The filtering member (28) thereby works in concert with the closable top of the container (10) and the generally vapor impermeable sides (14, 16, 18, 20) and base (12). It should be understood that while FIG. 1 depicts the filtering member (28) secured to the back side (18) of the container (10), usable containers can include filtering and/or deodorizing members secured to any portion of the interior, or simply deposited within the interior such that air carrying odors associated with contained waste will be affected by the filtering and/or deodorizing member. In other embodiments of the invention, the sides (14, 16, 18, 20) and/or base (12) of the container can also be provided with a scented or deodorizing compound.

Figure 2:
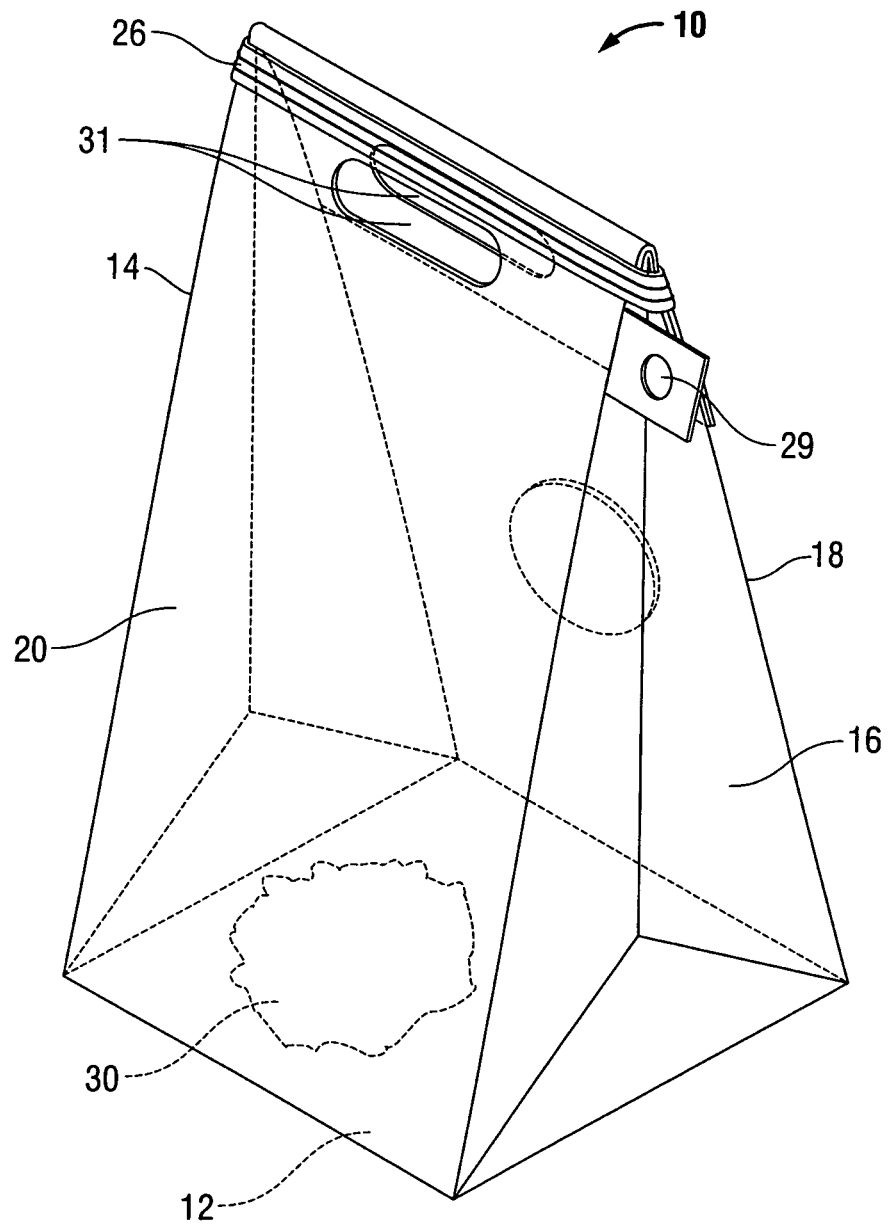
FIG. 2 depicts the container of FIG. 1 in a closed position.

Referring now to FIG. 2, the container (10) of FIG. 1 is depicted in a closed position. Specifically, animal waste (30) or a similar source of odor, such as human waste, clumped litter containing solid or liquid waste components, diapers, soiled pet pads or similar pet products, or other similar odorous objects, have been placed within the interior of the container (10). The top ends of the front side (20) and back side (18) of the container (10) have been placed into contact by at least partially folding the left and right sides (14, 16), and the closing member (26) has been rolled and/or folded downward such that the front and back sides (20, 18) are engaged therewith. The waste (30) and any odor associated therewith are thereby contained within the container (10) due to the vapor impermeability of the sides (14, 16, 18, 20) and base (12). The contained odors are further controlled by the filtering member (28). Prior to disposal, the rigidity of the base (12) permits the depicted container (10) to be placed in a freestanding orientation while containing the enclosed waste (30). In an embodiment of the invention, the container (10) can include an orifice (29), a handle (31), or combinations thereof disposed therethrough for ease in carrying, transport, and/or fastening of the container (10), as described previously.

Embodiments of the present invention thereby provide a container and method for storing human or animal waste, diapers, clumped cat litter, soiled pet products, and similar objects, and controlling associated odors by preventing exodus of odor from the container using multiple means of control, while enabling storage of the waste prior to disposal. Embodiments of the container described herein provide enhanced effectiveness for controlling odors when compared to similar inexpensive, disposable containers while remaining comparatively inexpensive and easy to produce and utilize.

While the present invention has been described with emphasis on certain embodiments, it should be understood that within the scope of the appended claims, the present invention can be practiced other than as specifically described herein.

What is claimed is:

1. A container for storing animal waste and controlling associated odor, the container comprising:

a compressible body comprising a base, a plurality of side surfaces, an open top, and an interior for containing an animal waste, wherein the interior of the compressible body comprises a contiguous enclosure comprising a material substantially impermeable to vapor to prevent permeation of an odor associated with the animal waste through the compressible body, wherein the material is foldable, compressible, or combinations thereof, for providing the compressible body with a compact shape for facilitating storage and an open shape for receiving the animal waste, and wherein the base and each of said plurality of side surfaces comprise contiguous surfaces defining the contiguous enclosure for physically blocking passage of the odor therethrough;

a closing member usable to engage a first side surface to at least one opposing side surface to secure the open top in a closed position to at least partially prevent exodus of air carrying the odor from the interior, wherein the closing member is positioned on said first side surface, wherein the closing member comprises a length greater than a width of said first side surface, wherein a first end of the closing member extends beyond the width of the first side surface in a first direction, wherein a second end of the closing member extends beyond the width of said first side surface in a second direction opposite said first direction, wherein the first and second ends are movable to contact said at least one opposing side surface and retain said at least one opposing side surface in contact with said first side surface;

a handle formed in said first side surface and said at least one opposing side surface, wherein the handle comprises a first elongated orifice formed in said first side surface below the closing member and the open top, and a second elongated orifice formed in said at least one opposing side surface below the closing member and the open top;

a filtering member secured to an interior surface of the base, said at least one side surface, or combinations thereof, wherein the filtering member at least partially removes the odor from the interior to minimize exodus of the odor from the compressible body; and a tab extending beyond a width of said at least one opposing side surface of the plurality of side surfaces, wherein the tab is independent of the closing member, and wherein the tab has a first orifice therethrough for receiving an external object to facilitate transport or storage of the container.

2. The container of claim 1, wherein the material of the compressible body comprises paper, plastic, rubber, aluminum, a textile material, or combinations thereof.

3. The container of claim 1, wherein the compressible body comprises an inner layer formed from the material substantially impermeable to vapor and an outer layer formed from an additional material that differs from the material substantially impermeable to vapor.

4. The container of claim 1, wherein the compressible body comprises at least one biodegradable material.

5. The container of claim 1, wherein the base is generally rigid for enabling the container to be placed in a freestanding orientation.

6. The container of claim 1, wherein the material of the compressible body is generally impermeable to liquid.

7. The container of claim 1, wherein the closing member comprises rubber, an elastic member, a flexible length of metal, a tie for rolling or compressing securing the open end of the compressible body into the closed position, at least one fastener usable to secure said first side surface to said at least one opposing side surface, or combinations thereof.

8. The container of claim 1, wherein the filtering member comprises a charcoal filter.

9. The container of claim 1, wherein the filtering member comprises a scented compound, a deodorizing compound, or combinations thereof.

10. The container of claim 1, wherein the material of the compressible body comprises a scented compound, a deodorizing compound, or combinations thereof.

11. The container of claim 1, wherein the base comprises a first width, and wherein the open top comprises a second width greater than the first width for accommodating at least partial entry of a scooping apparatus containing the animal waste into the interior.

12. The container of claim 11, wherein the first width is approximately one half the second width.

13. The container of claim 1, wherein the first elongated orifice and the second elongated orifice are alignable to receive an object therethrough.

14. The container of claim 1, wherein substantially all of the filtering member is disposed in contact with the interior surface.

15. A method for storing animal waste and controlling associated odor, the method comprising the steps of:

providing an animal waste into an upper opening of a container comprising a material substantially impermeable to vapor to prevent permeation of an odor associated with the animal waste through the container, wherein the container further comprises a base, a first side surface, and a second side surface, wherein the upper opening extends between respective upper edges of the first side surface and the second side surface, wherein at least one of the side surfaces has a tab comprising an orifice therethrough extending beyond a width of the at least one side surface, and wherein the base, the first side surface, and the second side surface comprise contiguous surfaces defining a contiguous enclosure for physically blocking passage of odor therethrough;

moving at least one of the first side surface and the second side surface toward the other of the first side surface and the second side surface, such that the first side surface contacts the second side surface;

moving a second portion and a third portion of a closing member, having a first portion secured to the first side surface, and a second portion and a third portion extending beyond a width of the first side surface to contact the second side surface and retain the first side surface in contact with the second side surface between the first portion and the second and third portions of the closing member;

permitting a filtering member secured to an interior surface of the base, the first side surface, the second side surface, or combinations thereof to at least partially remove the odor from the container to minimize exodus of the odor from the container;

transporting the container by inserting a hand through a first elongated orifice formed in said first side surface and through a second elongated orifice formed in said second side surface; and transporting the container utilizing an external object extending through the orifice of the tab.

16. The method of claim 15, wherein the step of providing animal waste into the container comprises transporting the animal waste using a scooping apparatus and passing the scooping apparatus through an open top of the container, wherein the open top comprises a width sized for accommodating the scooping device.

17. The method of claim 15, wherein the step of securing the container in the closed position comprises closing an open top of the container using a closing member, and wherein the closing member comprises rubber, an elastic member, a flexible length of metal, a tie for rolling or compressing securing the open end of the container into the closed position, at least one fastener usable to secure the first side surface to the second side surface, or combinations thereof.

18. The method of claim 15, wherein the step of permitting the filtering member within the container to at least partially remove the odor from the container comprises using a charcoal filter secured to an interior of the container to filter air within the container to remove odor associated with the animal waste.

19. The method of claim 15, wherein the step of permitting the filtering member within the container to at least partially remove the odor from the container comprises using a scented compound, a deodorizing compound, or combinations thereof, secured to an interior surface of the first side surface, the second side surface, the base, or combinations thereof.

20. The method of claim 15, further comprising the step of further removing the odor from the container using a scented compound, a deodorizing compound, or combinations thereof disposed on or within a body of the container.

21. The method of claim 15, wherein the container further comprises a generally rigid base, the method further comprising the step of storing the container in a freestanding orientation using the generally rigid base.

* * * * *